US00RE39885E

(19) United States
(12) Reissued Patent
Nadeau et al.

(10) Patent Number: US RE39,885 E
(45) Date of Reissued Patent: *Oct. 16, 2007

(54) DETECTION OF NUCLEIC ACID AMPLIFICATION

(75) Inventors: James G. Nadeau, Ellicott City, MD (US); George T. Walker, Chapel Hill, NC (US)

(73) Assignee: Becton, Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

This patent is subject to a terminal disclaimer.

(21) Appl. No.: 09/082,247

(22) Filed: May 20, 1998

Related U.S. Patent Documents

Reissue of:
(64) Patent No.: 5,547,861
Issued: Aug. 20, 1996
Appl. No.: 08/229,281
Filed: Apr. 18, 1994

(51) Int. Cl.
*C12Q 1/68* (2006.01)
*C12P 19/34* (2006.01)

(52) U.S. Cl. ..... 435/6; 435/91.2
(58) Field of Classification Search ..... 435/6, 435/91.2
See application file for complete search history.

(56) References Cited

U.S. PATENT DOCUMENTS

| | | | | | |
|---|---|---|---|---|---|
| 4,683,195 | A | * | 7/1987 | Mullis et al. | 435/6 |
| 4,965,188 | A | * | 10/1990 | Mullis et al. | 435/6 |
| 5,126,239 | A | | 6/1992 | Livak et al. | 435/6 |
| 5,200,314 | A | * | 4/1993 | Urdea | 435/6 |
| 5,210,015 | A | | 5/1993 | Gelfand et al. | |
| 5,348,853 | A | | 9/1994 | Wang et al. | 435/6 |
| 5,550,025 | A | | 8/1996 | Walker | |
| 5,567,583 | A | | 10/1996 | Wang et al. | 435/6 |
| 5,593,867 | A | | 1/1997 | Walker et al. | 435/91 |
| 5,712,386 | A | | 1/1998 | Wang et al. | 536/24.33 |
| 5,723,591 | A | | 3/1998 | Livak et al. | 536/22.1 |
| 5,763,181 | A | | 6/1998 | Han et al. | |

FOREIGN PATENT DOCUMENTS

| | | |
|---|---|---|
| EP | 0 420 260 | 4/1991 |
| WO | WO 90/06374 | 8/1990 |
| WO | WO 92/01812 | 2/1992 |
| WO | WO 92/02638 | 2/1992 |
| WO | WO 92/11390 | 7/1992 |
| WO | WO 92/18650 | 10/1992 |
| WO | WO 95/32306 | 11/1995 |

OTHER PUBLICATIONS

Walker et al, "A DNA Probe Assay Using Strand Displacement Amplification (SDA) and Filtration to Separate Reacted and Unreacted Detector Probes", Molecular and Cellular Probes, 9:399–402, 1995.
"Becton Dickenson Announces Licensing Agreement with Otsuka Pharmaceutical", http://www.newtech/sda/otsuka.html, 1998.
Letter from David W. Highet, Esq. of Becton Dickinson and Company dated Aug. 17, 1998.
G.T. Walker, et al. "Strand Displacement Amplification—An Isothermal, in vitro DNA Amplification Technique" *Nucl. Acids Res. 20*, 1691–1696 (1992).
G. T. Walker, et al. "Isothermal in vitro amplification of DNA by a restriction enzyme/DNA polymerase system" *Proc. Natl. Acad. Sci USA* 89, 392–396 (1992).
C.P.H. Vary "Triple–Helical Capture Assay for Quantification of Polymerase Chain Reaction Products" *Clin. Chem.* 38, 687–694 (1992).
J. Wahlberg, et al. "General Colorimetric Method for DNA Diagnostics Allowing Direct Solid–Phase Genomic Reactions" *Proc. Natl. Acad. Sci USA* 87, 6569–6573 (1990).
D.J. Kemp, et al. "Colorimetric Detection of Specific DNA Segments Amplified by Polymerase Chain Reactions" *Proc. Natl. Acad. Sci. USA* 86, 2423–2427 (1989).
F.F. Chehab, et al. "Detection of Specific DNA Sequences by Fluorescence Amplification: A Color Complementation Assay" *Proc. Natl. Acad. Sci. USA* 86, 9178–9182 (1989).
A.C. Syvanen, et al. "Quantification of Polymerase Chain Reaction Products by Affinity–Based Hybrid Collection" *Nucl. Acids Res.* 16, 11327–11338 (1988).
A. Chan, et al. "Quantification of Polymerase Chain Reaction Products in Agarose Gels with a Fluorescent Europium Chelate as Label and Time–Resolved Fluorescence Spectroscopy" *Anal. Chem.* 65, 158–163 (1993).
C.R. Newton, et al. "The Production of PCR Products with 5' Single Stranded Tails Using Primers that Incorporate Novel Phosphoramidite Intermediates" *Nucl. Acids. Res.* 21, 1155–1162 (1993).

(Continued)

*Primary Examiner*—Kenneth R. Horlick
*Assistant Examiner*—Joyce Tung
(74) *Attorney, Agent, or Firm*—Allan M. Kiang

(57) ABSTRACT

Methods for detecting, immobilizing or localizing primer extension products of a Strand Displacement Amplification reaction which are coupled to, and an indication of, amplification of the target sequence. The primer extension products are secondary, target-specific DNA products generated concurrently with SDA of the target sequence and can therefore be used to detect and/or measure target sequence amplification in real-time. In general, the secondary amplification products are not amplifiable and remain inert in the SDA reaction after they are formed without interfering with amplification of the target sequence. The secondary amplification products may be designed or modified to contain special features to facilitate their detection, immobilization or localization.

42 Claims, 3 Drawing Sheets

OTHER PUBLICATIONS

P.M. Holland, et al. "Detection of Specific Polymerase Chain Reaction Product by Utilizing the 5'–3' Exonuclease Activity of *Thermus Aquaticus* DNA Polymerase" *Clin. Chem.* 38, 462–463 (1992).

P.M. Holland, et al. "Detection of Specific Polymerase Chain Reaction Product by Utilizing the 5'–3' Exonnuclease Activity of *Thermus Aquaticus* DNA Polymerase" *Proc. Natl. Acad. Sci. USA* 88, 7276–7280 (1991).

WO9201812—Uhlen et al. Competitive PCR for quantitations of DNA, pp. 1–19, pub. Feb. 6, 1992.*

* cited by examiner

A' B' C' D' 5'
BIND SIGNAL PRIMER (R-B) AND SDA PRIMER A
EXTEND BOTH PRIMERS AND DISPLACE R-B EXTENSION PRODUCT
SDA AS USUAL TO PRODUCE PRIMARY TARGET
#6
#1
BIND SIGNAL PRIMER Q-C' AND SDA PRIMER D'
EXTEND PRIMERS, AND DISPLACE Q-C' EXTENSION PRODUCT
#2
BIND AND EXTEND R-B
#3
SECONDARY PRODUCT (DOUBLE-STRANDED)
#4
LINEAR AMPLIFICATION
BIND R-B AND EXTEND
#5

A' B' C' D' 5'
BIND SIGNAL PRIMER (R-B)
AND SDA PRIMER A
A' B' C' D'
A
B
R
EXTEND BOTH PRIMERS AND
DISPLACE R-B EXTENSION PRODUCT
#1
R B C D
BIND
SDA PRIMER D'
D'
R B C D
A' B' C' D'
A B C D
SDA AS USUAL TO
PRODUCE PRIMARY TARGET
EXTEND
PRIMERS
B' C' D'
R'
B' C' D'
R' R B C D
#2
LINEAR
AMPLIFICATION
BIND R-B
AND EXTEND
#3
B' C' D'
R' R B C D
SECONDARY
PRODUCT

DETECTION OF NUCLEIC ACID AMPLIFICATION

Matter enclosed in heavy brackets [ ] appears in the original patent but forms no part of this reissue specification; matter printed in italics indicates the additions made by reissue.

FIELD OF THE INVENTION

The present invention relates to methods for detecting and measuring amplification of a nucleic acid target sequence.

BACKGROUND OF THE INVENTION

In vitro nucleic acid amplification techniques have provided powerful tools for detection and analysis of small amounts of nucleic acids. The extreme sensitivity of such methods has lead to attempts to develop them for diagnosis of infectious and genetic diseases, isolation of genes for analysis, and detection of specific nucleic adds as in forensic medicine. Nucleic acid amplification techniques can be grouped according to the temperature requirements of the procedure. The polymerase chain reaction (PCR; R. K. Saiki, et al. 1985, Science 230, 1350–1354), ligase chain reaction (LCR; D. Y. Wu, et al. 1989, Genomics 4, 560–569; K. Barfinger, et al. 1990. Gene 89, 117–122; F. Barany. 1991. Proc. Natl. Acad. Sci. USA 88, 189–193) and transcription-based amplification (D. Y. Kwoh, et al. 1989. Proc. Natl. Acad. Sci. USA 86, 1173–1177) require temperature cycling. In contrast, methods such as strand displacement amplification (SDA; G. T. Walker, et al. 1992. Proc. Natl. Acad Sci. USA 89, 392–396 and G. T. Walker, et al. 1992. Nuc. Acids. Res. 20, 1691–1696, both disclosures being incorporated herein by reference), self-sustained sequence replication (3SR; J. C. Guatelli, et al. 1990. Proc. Natl. Acad. Sci. USA 87, 1874–1878) and the Qβ replicase system (P. M. Lizardi, et al. 1988. BioTechnology 6, 1197–1202) are isothermal reactions. In addition, WO 90/10064 and WO 91/03573 describe use of the bacteriophage phi29 replication origin for isothermal replication of nucleic acids.

A variety of methods have also been developed to detect and/or measure nucleic acid amplification. For the most part, these methods are primer-based, meaning that they depend on hybridization of a primer to the target sequence, in some cases followed by extension of the primer. Primer-based detection of amplified nucleic acids in PCR often relies on incorporation of an amplification primer into the amplified product (amplicon) during the amplification reaction. Features engineered into the PCR amplification primer therefore appear in the amplification product and can be used either to detect the amplified target sequence or to immobilize the amplicon for detection by other means. For example, Syvanen, et al. (1988. Nucleic Acids Res. 16, 11327–11338) report the use of biotinylated PCR amplification primers to produce biotin-containing amplification products. These amplicons can then be hybridized to a second probe containing a fluorescent dye or other reporter group. The hybridized complex is then selectively isolated from other components of the reaction mixture by affinity-based immobilization of the biotin-containing complex and is detected by means of the reporter group. Laongiaru, et al. (1991. European Patent Application No. 0 420 260) describe a similar use of biotin-containing PCR amplification primers conjugated to fluorescent dyes for detection of PCR amplification products. The amplicons containing the primers are separated from unextended primers on the basis of size, and multiplex amplification was detected using different fluorescent dyes on two amplification primer sets. Kemp, et al. (1989. Proc. Natl. Acad. Sci. USA 86, 2423–2427; 1990. PCT Patent Application No. WO 90/06374) describe a method for capturing amplified DNA by incorporation of one modified amplification primer and use of a second modified amplification primer as a means for detection. The Kemp "capture primer[ contains a 5' tail which is the single stranded form of the recognition sequence for the double-stranded DNA binding protein GCN4. The Kemp "detector primer" includes a biotin moiety on its 5' end. The amplified product is immobilized by binding to the double-stranded GCN4 recognition sequence generated by amplification using the capture primer. The biotin moiety introduced by the detector primer is bound to an avidin-peroxidase complex to provide colorimetric detection of the immobilized PCR amplification product. Wahlberg, et al. (1990. Proc. Natl. Acad. Sci. USA 87, 6569–6573) report a similar method in which one PCR amplification primer is biotinylated and the other contains a 5' tail encoding the E. coli lac operator sequence. Double stranded amplification products are immobilized by binding to streptavidin and detected colorimetrically by binding of a lac repressor-β-galactosidase fusion protein to the double-stranded lac operator generated by amplification. The Wahlberg, et al. method differs from the Kemp, et al. method in that the biotin-streptavidin interaction rather than the double-stranded binding protein provides immobilization of the amplification products and the double-stranded binding protein provides colorimetric detection. This suggests that the two methods could be combined by using two amplification primers, each with a 5' tail encoding the recognition sequence of a different double-stranded binding protein. Amplified products could then be immobilized by binding to one double stranded binding protein and detected by binding to the other. C. A. Vary (1992. Clinical Chemistry 38, 687–694; 1992. PCT Patent Application No. WO 92/11390) describes the use of amplification primers containing 5' tails which form hybridization sites for a third oligonucleotide when incorporated into otherwise double-stranded amplicons. Hybridization of one tail was used to capture the amplified product and the other was used to detect it by hybridization to a probe conjugated to a fluorescent dye.

All of these primer-based methods of detecting PCR amplification products require two amplification reactions to achieve high sensitivity, i.e., detection of fewer than 100 copies of the target sequence. That is, a first amplification of the target sequence is followed by a second amplification using nested primers incorporating the desired modifications for capture and/or detection. Two consecutive amplifications in this manner are needed to avoid unacceptably high levels of background signal produced by amplification of non-target DNA spuriously primed with the modified, signal-generating primers. This feature of the prior art methods makes them time-consuming and cumbersome, and the advantages of primer-based detection methods are therefore often offset by the requirement for a second consecutive amplification reaction.

Non-specific amplification of DNA would be expected to present particular problems for primer-based detection of amplification products in SDA reactions because these amplifications are carried out at a relatively low temperature (about 37°–40° C.) which would allow increased mispriming as compared to PCR, resulting in even higher levels of background signal. Unexpectedly, the instant methods for primer-based detection of SDA resulting in low levels of background signal in spite of the use of only a single amplification reaction which generates products for detection concurrently with amplification of the target sequence. Simultaneous or concurrent generation of a secondary amplification product and the amplified target sequence is referred to herein as real-time primer extension, real-time detection of amplification, etc.

SUMMARY OF THE INVENTION

The instant invention provides methods for detecting, immobilizing (capturing) or localizing primer extension products of an SDA reaction which are coupled to, and an indication of, amplification of the target sequence. The primer extension products are secondary, target-specific DNA products generated during SDA of the target sequence and can therefore be used to detect and/or measure target sequence amplification. The secondary products, however, are not amplifiable and remain inert in the SDA reaction after they are formed without interfering with the exponential amplification of the target sequence. The secondary product can be designed or modified to contain special features to facilitate its detection, immobilization (capture) or localization. The inventive methods are useful for real-time monitoring of SDA reactions, especially in situations where detection of target sequence amplicons would interfere with further amplification or manipulation. The instant methods will also be useful for detection of amplification products in fixed cells after in situ SDA, especially when the secondary products contain 5' tail sequences to facilitate detection or localization of amplification products.

DESCRIPTION OF THE DRAWINGS

FIG. 1A illustrates the production of the secondary amplification product from a single stranded target sequence using two signal primers. FIG. 1B shows the analogous process originating from the complementary strand when the original target sequence is double stranded.

DETAILED DESCRIPTION OF THE INVENTION

Figure 1A:
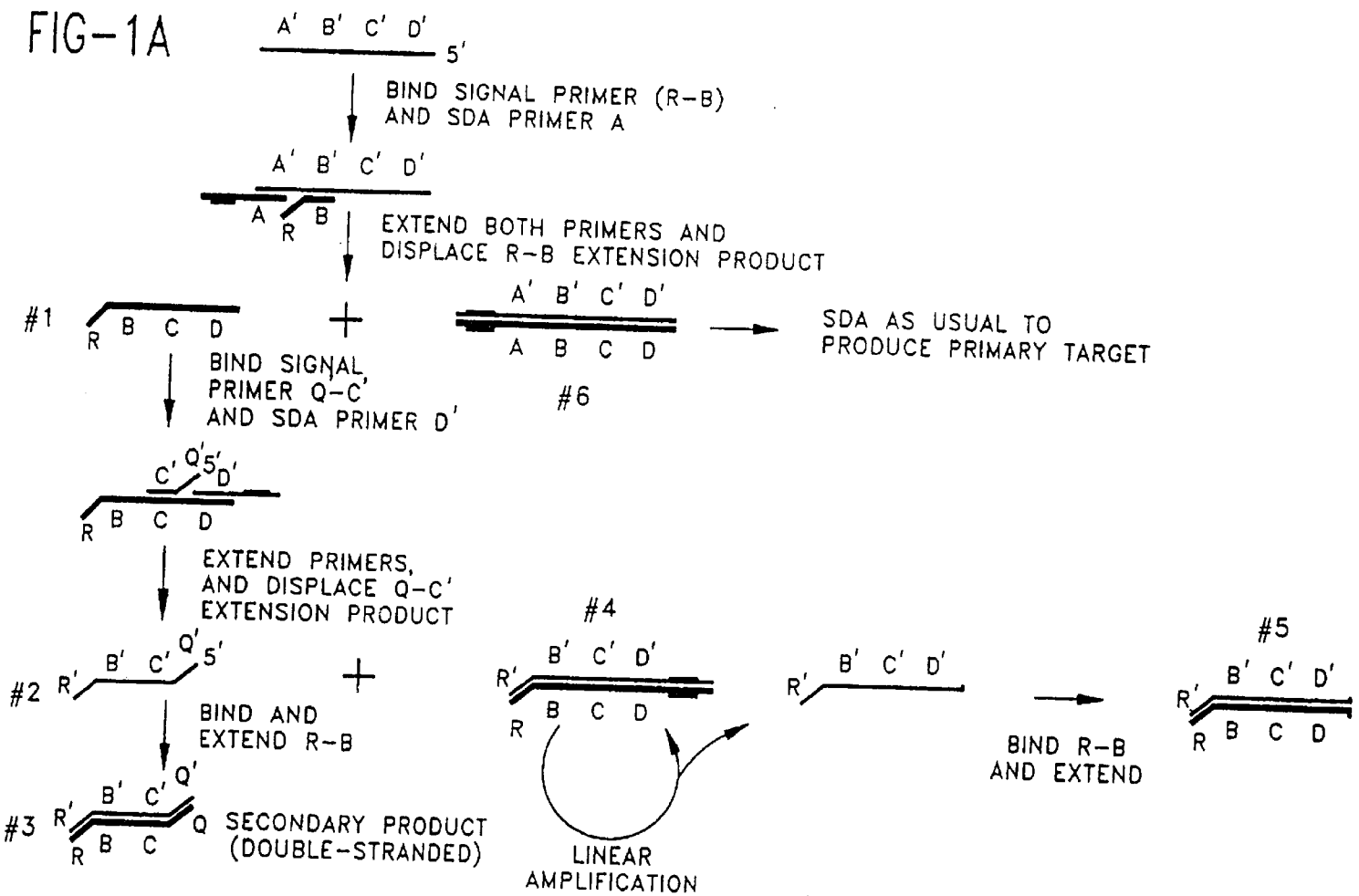
FIG. 1A and FIG. 1B illustrate the steps of the methods of the invention.

The present invention is a method for detecting, monitoring or localizing amplification products of SDA reactions by real-time primer extension. Amplification of a target sequence by SDA is detected, monitored or localized by simultaneously generating a secondary amplification product, the production of which is tightly coupled to amplification of the target sequence. This secondary amplification product is produced during the SDA reaction without requiring any additional additional amplification steps or manipulations. Once generated, the secondary amplification product is inert in the reaction mixture and does not interfere with or inhibit normal SDA of the desired target sequence. The methods are therefore useful for real-time monitoring of SDA and detecting amplification of the target sequence, especially in situations where detection of the amplified target sequence itself would inhibit or prevent further reaction or manipulation of the amplicons.

The present invention provides a primer-based amplification detection method in which the need for a second amplification reaction is eliminated. The method employs signal primers which are similar to capture and detector probes and do not function as amplification primers in the SDA reaction. Consequently, any extension products formed through errant extension of these signal primers on non-target templates cannot undergo subsequent amplification. Because misprimings itself is comparatively rare, it is detectable only after subsequent amplification of the misprimed sequence. In the absence of such subsequent amplification, as in the methods of the present invention, the signal primers may be added to the amplification reaction prior to initiation of amplification with no apparent increase in background signal levels. This greatly simplifies the detection procedure and makes possible homogeneous real-time analysis of SDA reactions.

As used herein, the following terms and phrases are defined as follows:

An amplification primer is a primer for amplification of a target sequence by primer extension. For SDA, the 3' end of the amplification primer (the target binding sequence) hybridizes at the 3' end of the target sequence. The amplification primer comprises a recognition site for a restriction endonuclease near its 5' end. The recognition site is for a restriction endonuclease which will cleave one strand of a DNA duplex when the recognition site is hemimodified ("nicking"), as described by Walker, et al. (1992. PNAS, supra). A hemimodified recognition site is a double stranded recognition site for a restriction endonuclease in which one strand contains at least one derivatized nucleotide which causes the restriction endonuclease to nick the primer strand rather than cleave both strands of the recognition site. Usually, the primer strand of the hemimodified recognition site does not contain derivatized nucleotides and is nicked by the restriction endonuclease. Alternatively, the primer may contain derivatized nucleotides which cause the unmodified target strand to be protected from cleavage while the modified primer strand is nicked. The preferred hemimodified recognition sites are hemiphosphorothioated recognition sites for the restriction endonucleases HincII, HindII, AvaI, NciI and Fnu4HI. The amplification primer also comprises a 3'-OH group which is extendable by DNA polymerase when the target binding sequence of the amplification primer is hybridized to the target sequence. For the majority of the SDA reaction, the amplification primer is responsible for exponential amplification of the target sequence.

Extension products are nucleic acids which comprise a primer and a newly synthesized strand which is the complement of the target sequence downstream of the primer binding site. Extension products result from hybridization of a primer to a target sequence and extension of the primer by polymerase using the target sequence as a template.

A bumper primer is a primer which anneals to a target sequence upstream of the amplification primer, such that extension of the bumper primer displaces the downstream amplification primer and its extension product. Extension of bumper primers is one method for displacing the extension products of amplification primers, but heating is also suitable.

Identical sequences will hybridize to the same complementary nucleotide sequence. Substantially identical sequences are sufficiently similar in their nucleotide sequence that they also hybridize to the same partially complementary nucleotide sequence.

The terms target or target sequence refer to nucleic acid sequences to be amplified. These include the original nucleic acid sequence to be amplified, its complementary second strand and either strand of a copy of the original sequence which is produced in the amplification reaction. The target sequence may also be referred to as a template for extension of hybridized amplification primers.

A signal primer is a primer which hybridizes to a target sequence downstream of an amplification primer such that extension of the amplification primer displaces the signal primer and its extension product. The signal primer comprises a 3'-OH group which can be extended by DNA polymerase when the signal primer is hybridized to the target sequence. The signal primer may be unmodified, e.g., for detection of secondary amplification products based on their size. Alternatively, the signal primer may include a reporter group or label, or a structural feature to facilitate detection of its extension product.

Amplification products, amplified products or amplicons are copies of the target sequence generated by hybridization and extension of an amplification primer. This term refers to both single stranded and double stranded amplification primer extension products which contain a copy of the original target sequence, including intermediates of the amplification reaction.

Secondary amplification products or secondary products are copies of the target sequence generated by hybridization and extension of a signal primer. The secondary amplification product comprises an internal segment of the amplified target sequence. These terms also refer to both single stranded and double stranded extension products of signal primers, including intermediates in the process which generates the final double stranded form. In contrast to amplification products, the double stranded secondary amplification product is generally not available for further amplification, although some secondary amplification products may be amplifiable in a linear fashion.

In the methods of the invention, amplification primers for SDA are hybridized to a target sequence and the target sequence is amplified generally as described by Walker, et al., 1993 PNAS or Walker, et al. 1993 Nuc. Acids Res., supra. As described in these two publications, the target sequence may be prepared for SDA either by restricting total DNA with an appropriate restriction endonuclease (e.g., HincII) or by generating target fragments having the appropriate restriction endonuclease recognition sites at the ends using bumper primers and amplification primers. Prepared fragments containing the target sequence are then amplified by SDA as described. However, the SDA reaction of the invention further comprises at least one signal primer which results in simultaneous or concurrent generation of a secondary amplification product for use in detecting, monitoring or localizing amplification products produced by the SDA reaction. The secondary amplification products may also contain features which facilitate their capture or immobilization, so that they may be isolated for detection, quantitation or further manipulation. The secondary amplification products are produced in the SDA reaction by inclusion of at least one signal primer in the reaction mixture. For certain applications, it may be preferable to include a pair of signal primers. The signal primer or signal primers hybridize to the target sequence downstream of the hybridization site of the amplification primers. They are extended by polymerase in a manner similar to extension of the amplification primers. The signal primer hybridizes at a site in the target sequence such that extension of the amplification primer displaces the extension product of the signal primer. At least the 3' end of the signal primer comprises a sequence which hybridizes to the target sequence. The entire signal primer may hybridize to the target sequence, for example when it is unmodified or chemically modified for detection by addition of a reporter group, label or affinity ligand. Alternatively, the 5' end of the signal primer may comprise a sequence which does not hybridize to the target sequence but which contains special nucleotide sequences (often involving structural features) which facilitate detection or capture of the secondary amplification product. These chemical modifications and special sequences are incorporated into the secondary amplification products when the signal primers are hybridized and extended on a template. Examples of chemical modifications include affinity ligands (e.g., avidin, streptavidin, biotin, haptens, antigens and antibodies) and reporter groups (labels, e.g., radioisotopes, fluorescent dyes, enzymes which react to produce detectable reaction products, and visible dyes). Examples of special nucleotide sequences include (i) sequences which will form a triple helix by hybridization of a labeled oligonucleotide probe to the double stranded secondary amplification product, and (ii) recognition sites for double-stranded DNA binding proteins which become capable of binding the double-stranded DNA binding protein when rendered double stranded during amplification (e.g., repressors, regulatory proteins, restriction endonucleases, RNA polymerase). Nucleotide sequences which result in double stranded restriction endonuclease recognition sites are a preferred structural feature for use in signal primers, as subsequent restriction may be used to generate a secondary amplification product which is recognizable by a characteristic size.

Figure 1B:
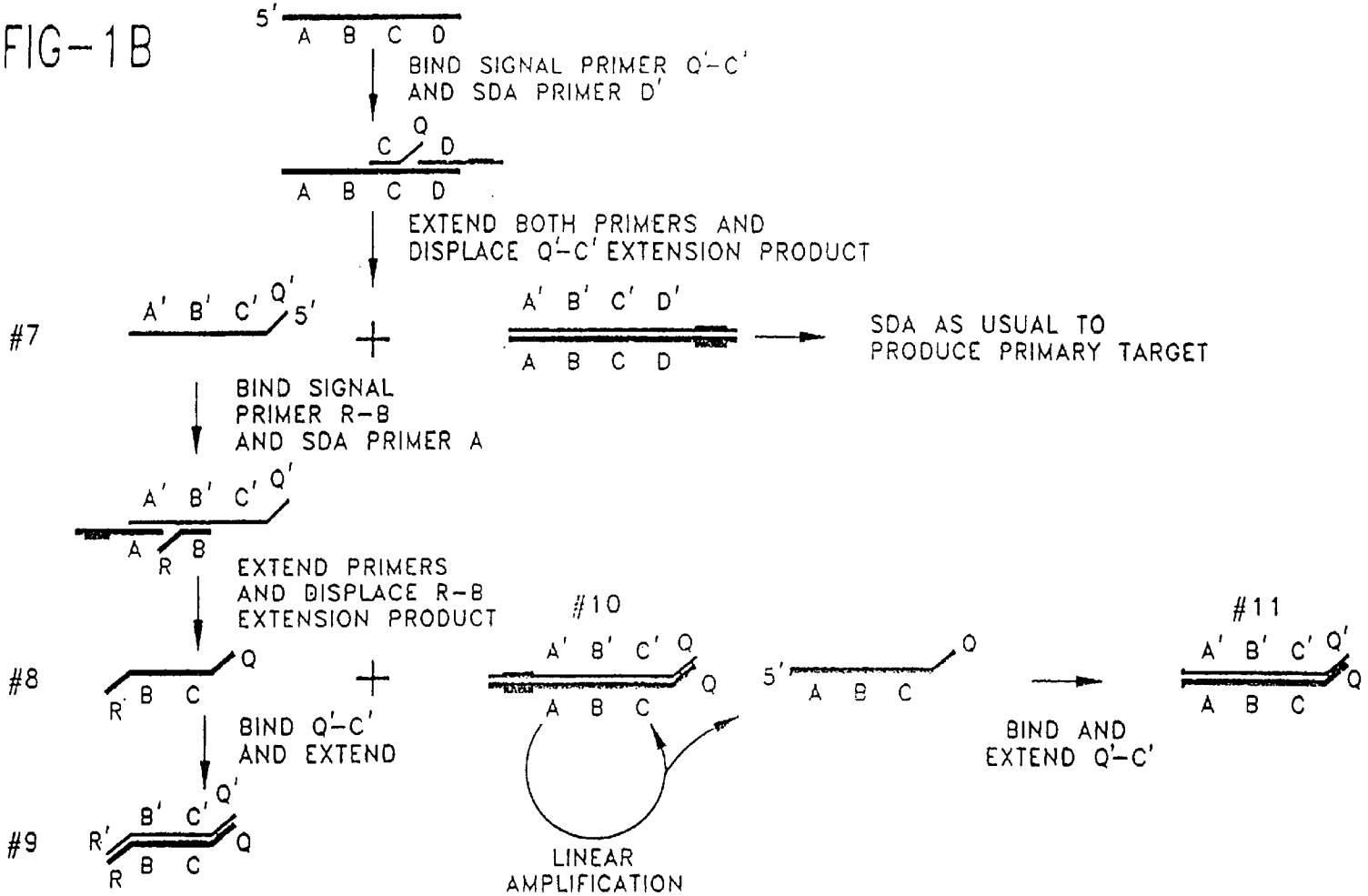

When the inventive methods employ two signal primers which hybridize to opposite strands of a double stranded target sequence, as illustrated in FIGS. 1A and 1B, one of the signal primers may contain a special nucleotide sequence or chemical modification to facilitate capture or immobilization of the secondary amplification product and the other may contain a detectable reporter group or label for detection of the captured or immobilized secondary amplification product. The use of labels and reporter groups for detecting nucleic acids as well as the use of ligands, chemical modifications and nucleic acid structural features for capture or immobilization of nucleic acids is well known in the art. Alternatively, the signal primer may be unmodified, i.e., without reporter groups, capture groups or structural features to facilitate detection or capture of the secondary amplification products. The secondary amplification products may then be detected based on their size, e.g., by gel electrophoresis and ethidium bromide staining. All of these methods are useful in the present invention and one skilled in the art can routinely select appropriate methods for use in any particular amplification assay system.

It is an important feature of the invention that the signal primers do not function as amplification primers in the SDA reaction in which they are employed. Without wishing to be bound by any specific mechanism by which the inventive methods work. Applicants believe it is this feature which allows the signal primers to be added to the amplification reaction mixture without promoting the high levels of background signal generated by other primer-based methods. High levels of background signal are believed to be due to non-specific priming and subsequent amplification of spuriously primed non-target DNA when the primers are capable of functioning as amplification primers. The present invention therefore greatly simplifies the procedures for primer-based detection methods, which previously relied on two consecutive amplification reactions to attain high sensitivity and specificity, the second reaction being performed with internally nested signal-generating amplification primers.

As stated above, nucleic acid fragments having appropriate restriction endonuclease recognition sequences at the ends and containing the target sequence may be prepared for amplification either as described by Walker, et al. 1992. PNAS, supra or as described by Walker, et al. 1992 Nuc. Acids Res., supra. For simplicity, the illustrations of the inventive methods in FIG. 1A, FIG. 1B and FIG. 2 begin with a nucleic acid fragment containing the target sequence. If prepared according to Walker, et al. 1992. PNAS, supra, it represents restricted double stranded DNA which has been denatured. If prepared according to Walker, et al. 1992. Nuc. Acids Res., supra, appropriate restriction endonuclease recognition sites are added to the fragment according to the disclosed target generation scheme. It is believed that bumper, amplification and signal primers may simultaneously hybridize to a target sequence in the target generation scheme of Walker, et al. (1992. Nuc. Acids Res., supra), extension of each upstream primer displacing the extension product of the downstream primer and simultaneously generating amplifiable target fragments and secondary amplification products.

FIG. 1A and FIG. 1B illustrate one embodiment of the invention in which a pair of signal primers are used for detecting amplification of a double-stranded target sequence (5'-A-B-C-D/5'-D'-C'-B'-A'). FIG. 1A illustrates the method of the invention for the first of the two complementary strands of the target sequence (5'-D'-C'-B'-A'). The raised portion of the amplification primers illustrated in FIGS. 1A, 1B and 2 indicates a nickable restriction endonuclease recognition site as described above and by Walker, et al. (1992. PNAS and Nuc. Acids Res.). Long raised portions illustrate full-length restriction endonuclease recognition sites and short raised portions illustrate partial restriction endonuclease recognition sites, generally produced alter nicking and displacing a strand. The nucleic acid fragments comprising the target sequence may be generated either by endonuclease restriction of larger nucleic acids (Walker, et al. 1992. PNAS, supra) or by target generation as described by Walker, et al. (1992. Nuc. Acids Res., supra). However, for purposes of illustration and to simplify the diagrams, FIGS. 1A, 1B and 2 begin with the target sequence contained on a nucleic acid fragment previously restricted with a restriction endonuclease which does not cut the target sequence.

In FIG. 1A, signal primer R-B is included in the SDA reaction mixture and hybridizes to the target sequence downstream of a first amplification primer by hybridization of the B portion of the signal primer to B'. The R portion of the R-B signal primer sequence includes a reporter group or label, or is a structural feature to facilitate detection or capture. R may or may not hybridize, as discussed above, but is shown here as not hybridizing to clarify the different functional features of the signal primer. For the purposes of this illustration, R will contain a reporter group, but may contain other chemical modifications or structural features as discussed above. Both amplification primer A and signal primer R-B are extended by DNA polymerase using the target sequence as a template. The signal primer extension product R-B-C-D (structure #1) is displaced from the template by extension of amplification primer A and in turn serves as a template for hybridization and extension of a second signal primer Q'-C' and a second amplification primer D'. The C' portion of the Q'-C' sequence hybridizes to C. The Q' portion of the second signal primer is analogous to R, and for purposes of this illustration Q' will contain a modification or sequence to facilitate capture of the secondary amplification product. The Q'-C' extension product is displaced by extension of the second amplification primer. The displaced Q'-C' extension product (structure #2) then serves as a template for hybridization and extension of R-B, resulting in a double stranded, target-specific secondary amplification product (structure #3) which comprises the terminal segment (R and Q') of the signal primers and the internal segment B'-C' of the target sequence. As the secondary amplification product does not contain nickable restriction endonuclease recognition sites, it is not amplifiable in the SDA reaction and remains effectively inert throughout the remainder of the amplification reaction, but additional copies of the secondary amplification product are generated from the target sequence.

Hybridization and extension of the second amplification primer (D'), in addition to displacing the R'-B'-C'-Q' extension product, generates a double stranded fragment with the R/R' sequence at one end and a hemimodified restriction endonuclease recognition site at the other end (structure #4). This restriction endonuclease recognition site is nickable by the restriction endonuclease present in the SDA reaction. The DNA polymerase present in the SDA reaction can then initiate polymerization and displacement at the nick, resulting in the illustrated R'-B'-C'-D' product comprising a portion of the restriction endonuclease recognition site. This product can be made double-stranded by hybridization and extension of R-B (structure #5). Although cyclically repeating the nicking, polymerizing and displacing cycle amplifies this fragment at a linear rate, generally neither the single-stranded or double-stranded product will be detectable by virtue of the absence of the Q/Q' portion containing the modification or sequence to facilitate capture. If the functions of Q/Q' and R/R' are reversed, (i.e., Q/Q' contains the reporter group or label and R/R' contains the modification or sequence to facilitate capture), these products, though captured, would not be detectable by virtue of the absence of the reporter group or label. It should be understood, however, that structure #5 may be detectable when the reporter group is detectable independent of capture, e.g., when the reporter group is a fluorescent label detectable by anisotropy or fluorescence polarization (WO 92/18650; R. Devlin, et al. 1993. Clin. Chem. 39, 1939–1943) or a radioisotope which can be detected by gel electrophoresis and autoradiography.

FIG. 1A also shows how extension of the first amplification primer on the target sequence, in addition to displacing the extension product of R-B, generates the double-stranded target sequence with the hemimodified, nickable restriction endonuclease recognition site which is required for amplification of the target sequence by SDA (structure #6). These reaction products enter the conventional SDA reaction and are amplified. Formation of the secondary amplification product is therefore tightly coupled to amplification of the target sequence and is useful to monitor whether or not amplification has taken place as well as to provide a measure of target amplification. In spite of the tight linkage of generation of the secondary amplification product and generation of amplification products, however, amplification of the target sequence is not inhibited provided essential reaction components are present in excess. In addition, amplified target sequences may also bind signal primers, resulting in generation of additional copies of the secondary amplification products.

FIG. 1B illustrates generation of secondary amplification products from the complementary second strand of the double-stranded target sequence (5'-A-B-C-D). In general, the reaction steps for the complementary second strand are similar to those for the first strand. However, the second amplification primer (D') and signal primer C'-Q' hybridize first to the complementary strand and are extended. The first amplification primer (A) and signal primer R-B then hybridize to the displaced extension product of C'-Q' (A'-B'-C'-Q', structure #7) and are extended to produce R-B-C-Q (structure #8). Hybridization of Q'-C' to R-B-C-Q and extension results in the double stranded secondary amplification products R'-B'-C'-Q'/R-B-C-Q (structure #9). This secondary amplification product is detectable in systems requiring both capture and reporter groups due to the presence of both features in structure #9. The reaction for the complementary strand also produces a reaction product which can be linearly amplified by nicking, polymerizing and displacing (structure #10). The displaced single strand of this linear amplification becomes double stranded by hybridization and extension of Q'-C' (structure # 11). Generally, neither the single or double stranded reaction products of this linear amplification are detectable due to the absence of either the reporter group or the capture group. They are not further amplifiable because they lack an intact restriction endonuclease recognition site. However, if Q comprises a reporter group which is detectable independent of capture (e.g., a fluorescent label or a radioisotope as described above), structures # 10 and # 11 will also be detectable.

Figure 2:
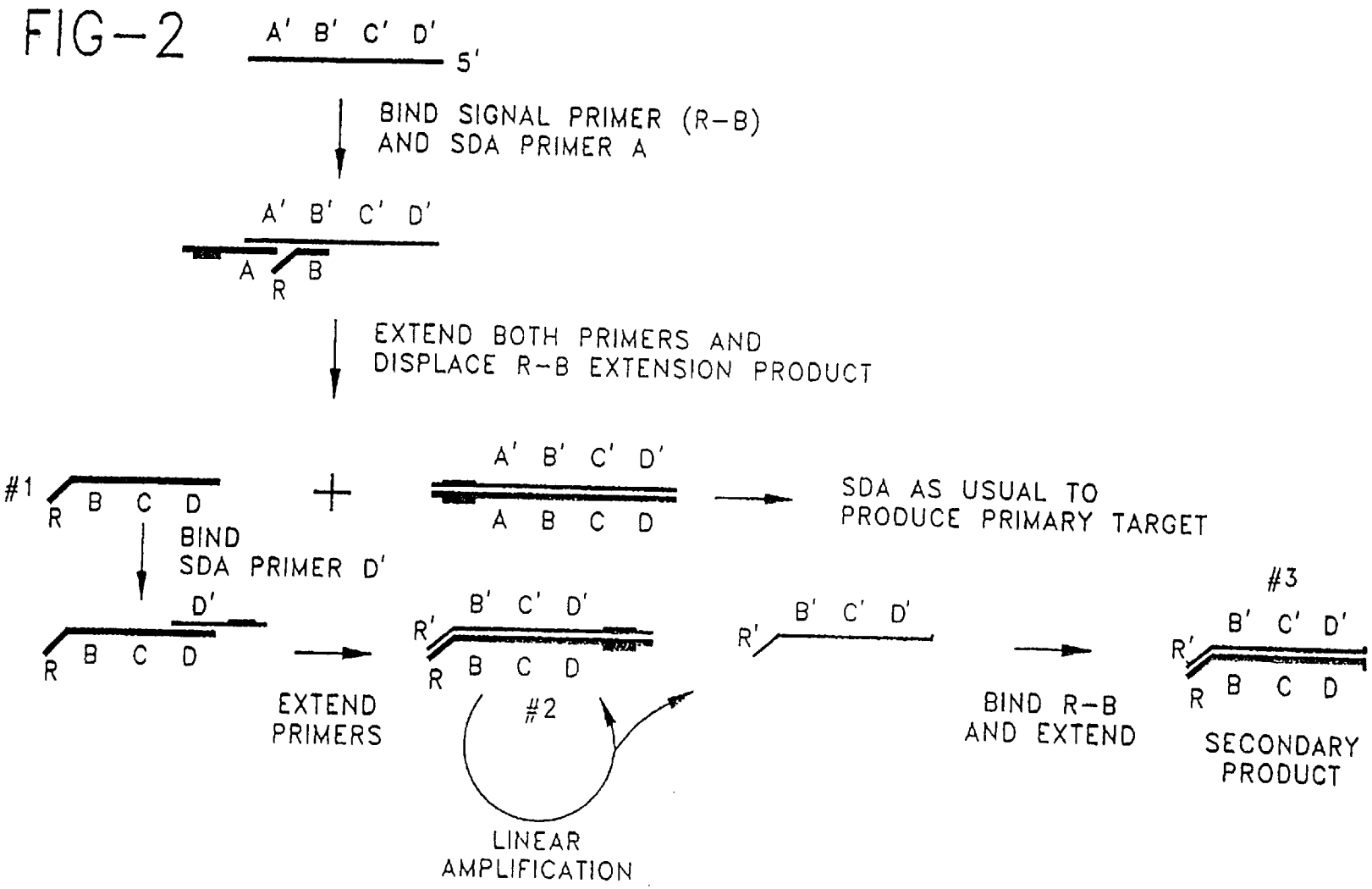
FIG. 2 illustrates the production of the secondary product using a single signal primer.

Detection specificity will generally be improved when two signal primers are employed as in FIG. 1A and FIG. 1B, but a single signal primer may also be used. This method is illustrated in FIG. 2. In this case, the signal primer may contain either a capture group or a reporter group, and the target sequence itself or an amplification primer may optionally provide a second capture or reporter group. Alternatively, when both a capture and reporter group are required, the signal primer may contain both a capture and a reporter, group which act in conjunction only when the signal oligonucleotide becomes double-stranded. This structure is formed only when the presence of target sequences induces priming, extension, displacement and re-priming as shown in FIG. 2. Such bi-functional signal primers may also form the basis for a variety of homogeneous detection methods such as fluorescence anisotropy or fluorescence energy transfer.

To generate secondary amplification products using a single signal primer according to FIG. 2, a first amplification primer (A) and the signal primer R-B are hybridized to a single stranded target sequence A'-B'-C'-D'. Both primers are extended, and extension of the first amplification primer displaces the extension product of signal primer R-B (R-B-C-D), producing structure #1. As there is no second signal primer, only the second amplification primer (D') hybridizes to P-B-C-D and is extended, generating structure #2 with a nickable, hemimodified restriction endonuclease recognition site. Linear amplification of this product by nicking, polymerizing and displacing, as shown, generates fragments to which the signal primer can hybridize and be extended. This generates the double stranded secondary amplification product, structure #3. It is not amplifiable due to the lack of an intact restriction endonuclease recognition site, but is detectable by virtue of R/R' when the reporter or capture group is detectable only in double stranded form or by virtue of R when the reporter group is detectable alone. When detection of the reporter group does not require double-strandedness (e.g., a fluorescent label), structures #1, #2 and #3 are detectable as secondary amplification products.

EXAMPLE 1

The real-time detection of amplification of the instant invention was compared to conventional post-amplification detection of amplified target sequences. Fragments of the IS6110 sequence of Mycobacterium tuberculosis (M.tb) were amplified in SDA reactions performed essentially as described by Walker, et al. (1992, Nuc. Acids Res.), except that each 60 μL reaction mixture contained 0.2 μg of human placental DNA and varying amounts of genomic M.tb DNA. Amplification primer sequences ($S_1$ and $S_2$) and bumper primer sequences ($B_1$ and $B_2$) were also as in Walker, et al. (1992, Nuc. Acids Res.) For the amplification reactions incorporating signal primers, the $^{32}$P-labeled signal primer $^{32}$P-CGTTATCCACCATAC (SEQ ID NO:1) was added to the reactions prior to amplification at a final concentration of 60 nM. Predicted secondary amplification products produced in these reactions were 35 and 56 nucleotides in length. For post-amplification detection of amplified target sequences, one-tenth of the reaction mixture was used to detect amplification products by primer extension of SEQ ID NO:1 as described by Walker, et a. (1992, Nucl. Acids. Res., supra), producing extension products either 35 or 56 nucleotides in length.

Amplification was allowed to proceed for 2 hr. at 37° C. in the presence of 1 to 500,000 genome copies of M.tb. After stopping the amplification, one-tenth of each reaction was subjected to electrophoresis on denaturing polyacrylamide gels. As little as one copy of M.tb genomic DNA was detected using the signal primer according to the invention. Also, the signal intensity decreased with decreasing target levels, indicating that the levels of secondary amplification product reflect the degree of target sequence amplification. The real-time extension of the signal primer appeared on the gel to be several fold less sensitive than the conventional post-amplification primer extension method, possibly because the $^{32}$P-labeled signal primer was present during SDA at concentrations about 10-fold less than the SDA primers. If SDA primers are extended on the target sequence before a signal primer binds and is extended, no signal will result. Thus, higher concentrations of signal primer should increase the method's sensitivity by improving hybridization kinetics for the signal primer. Higher signal primer concentrations are therefore preferred when reaction products are separated for detection, but the concentration of amplification primers may be kept similar to the concentrations used in conventional SDA. However, lower signal primer concentrations are preferred to keep background low for homogeneous detection methods such as fluorescence anisotropy. The lower concentrations of signal primer are preferably used with lower concentrations of polymerase and the amplification primer which hybridizes upstream of the signal primer than is customary in conventional SDA. This experiment also demonstrated that the presence of the signal primer in the amplification reaction mixture does not lead to significant levels of background signal. In fact, background signal levels appeared to be lower in samples detected by real-time signal-primer extension as compared to post-amplification primer extension.

EXAMPLE 2

SDA reactions were performed generally as previously described (Walker, 1993, PCR—Methods and Applications 3. 1) in 50 mM $KiPO_4$ (pH 7.5), 0.1 mg/mL bovine serum albumin, 0.5 mM dUTP, 0.2 mM each dGTP, dCTP and dATPαS, 7 mM $MgCl_2$, 11% (v/v) glycerol, the indicated concentrations of amplification primers, 25 nM bumper primers, 50 ng human placental DNA, the indicated amount of exonuclease deficient Klenow (United States Biochemicals), 150 units HincII (New England Biolabs). Reactions were run for the indicated time at 41° C. SDA reactions contained varying amounts of M.tb DNA, which contains the IS6110 target sequence for amplification. The $S_1$ amplification primer sequence, the $B_1$ bumper primer sequence and the $B_2$ bumper primer sequence used were as described by Walker, et al. (1992, Nuc. Acids Res., supra). The $S_2$ amplification primer (SEQ ID NO:2) had the target binding sequence and HincII site disclosed by these authors, but comprised a different sequence at the 5' end. The amplification primers hybridize to nucleotide positions 972–984 and 1011–1023 of the IS6110 sequence. The bumper primers hybridize to nucleotide positions 954–966 and 1032–1044. Secondary amplification products were visualized by autoradiography after electrophoresis on denaturing polyacrylamide gels.

SDA reactions were performed for 3 hrs. in the presence of 0.1 nM of a 5'-$^{32}$P-labeled signal primer (SEQ ID NO:3). This signal primer is 28 nucleotides in length and hybridizes to nucleotide positions 985–1012 of the IS6110 target sequence, between the amplification primers. $S_1$ and $S_2$ were present at 180 and 30 nM, respectively. Exonuclease deficient Klenow was used at 0.25 units. Samples 1–4 contained 100, 10, 1 and 0 M.tb genome molecules, respectively. During the SDA reaction, SEQ ID NO:3 is extended by polymerase to a length of 44 nucleotides using the target sequence as a template. As discussed above, this template is most likely primarily the displaced, amplified target strand generated during SDA, but concurrent extension of the bumper, amplification and signal primers on the original target sequence has not been ruled out and would be expected to occur as well. The 44-mer is displaced from the target sequence by extension of the upstream amplification primer ($S_2$). The 3'-end of the 44-mer hybridizes to the 3'-end of the second amplification primer ($S_1$) and a double-stranded 65-mer is formed after extension by polymerase. The 44-mer and 65-mer secondary amplification products were observed only in the presence of the M.tb target sequence (samples 1–3), indicating signal primer extension and transformation to double stranded form.

The preceding SDA reactions were repeated in the presence of 0.1 nM (samples 1–3) or 1 nM (samples 4–6) of a 5'-$^{32}$-P-signal primer which was 15 nucleotides in length (SEQ ID NO:4). This signal primer hybridizes at nucleotide positions 999–1013 of the IS6110 target sequence, between the amplification primers. $S_1$ and $S_2$ were used at 500 nM. Two units of exonuclease deficient Klenow were used and SDA was performed for 2 hrs. The three nucleotides at the 5'-end of SEQ ID NO:4 and the three nucleotides at the 3'-end of SEQ ID NO:2 (the $S_2$ amplification primer) are identical and therefore compete for the same IS6110 binding site. Samples 1 and 4 contained 10000 M.tb genome molecules while samples 2 and 5 contained 100 genome molecules. Samples 3 and 6 did not contain M.tb DNA.

During the SDA reaction, 45-mer and 66-mer secondary products are produced when the target sequence is amplified. They were observed only in the presence of M.tb DNA, indicating extension of the signal primer and transformation into double stranded form (samples 1, 2, 4 and 5). In the absence of M.tb DNA (samples 3 and 6), no radiolabeled products were seen. More sensitive detection was obtained when using a concentration of 1 nM of signal primer (samples 4–6) as compared to 0.1 nM, most likely due to more favorable hybridization kinetics for the signal primer and improved thermodynamic stability of the signal primer/target sequence hybrid during SDA.

SDA was repeated in the presence of 0.1 nM of a 5'-$^{32}$P-labeled signal primer which was 42 nucleotides in length (SEQ ID NO:5). The 26 nucleotides at the 3'-end of the signal primer (the target binding sequence) hybridize to the IS6110 target sequence at nucleotide positions 985–1010, between the amplification primers. 5' to the target binding sequence is a recognition site for the restriction endonuclease HincII. $S_1$ and $S_2$ were present at 180 and 30 nM. Exonuclease deficient Klenow was used at 0.25 units and SDA was performed for 3 hrs. Samples 1–4 contained 100, 10, 1 and 0 M.tb genome molecules.

During the SDA reaction, the signal primer is extended by the polymerase to a length of 58 nucleotides. This 58-mer is displaced by extension of the upstream amplification primer (SEQ ID NO:2). The 3'-end of the 58-mer hybridizes to the 3'-end of the other amplification primer ($S_1$), forming a double-stranded 79-mer after extension by polymerase. The HincII recognition site at the 5'-end of the signal primer becomes cleavable by HincII upon formation of the double-stranded 79-mer. That is, in the double-stranded 79-mer, both the strand comprising the original signal primer and the strand formed through polymerase extension using dGTP, dCTP, TTP and dATPαS are cleavable. HincII does not cleave the signal primer in its original single-stranded form. Cleavage of the double stranded 79-mer during the SDA reaction produces a 5'-$^{32}$P-labeled 13-mer which is detectable as a secondary amplification product.

58-mer and 79-mer primer extension secondary amplification products and the 13-mer cleavage secondary amplification product were observed only in the presence of M.tb target DNA (samples 1–3), indicating extension of the signal primer and transformation to double-stranded form. In the absence of M.tb DNA no secondary amplification products (extension products or cleavage products) were observed.

SDA was repeated in the presence of 0.1 nM of a 5'-$^{32}$P-labeled signal primer which was 33 nucleotides in length (SEQ ID NO:6). The 26 nucleotides at the 3'-end of the signal primer (the target binding sequence) hybridize to the IS6110 target sequence at nucleotide positions 985–1010, between the amplification primers. 5' to the target binding sequence is a recognition site for the restriction endonuclease EcoRI. $S_1$ and $S_2$ were present at 180 and 30 nM, respectively. Exonuclease deficient Klenow was used at 0.25 units. SDA was performed for 3 hrs. Samples 1–4 contained 100, 10, 1 and 0 M.tb genome molecules. After SDA, 20 units of EcoRI were added to each SDA reaction and the samples were incubated for 30 min. at 37° C.

During the SDA reaction, the signal primer is extended by the polymerase to a length of 49 nucleotides. This 49-mer is displaced by extension of the upstream amplification primer (SEQ ID NO:2). The 3'-end of the 49-mer hybridizes to the 3'-end of the other amplification primer ($S_1$), forming a double-stranded 70-mer after extension by polymerase. The EcoRI recognition site at the 5'-end of the signal primer becomes cleavable by EcoRI upon formation of the 70-mer and addition of EcoRI. EcoRI cleavage of the double-stranded 70-mer produces a cleavage product which is a 5'-$^{32}$P-labeled dinucleotide. This dinucleotide is detectable by autoradiography as a secondary amplification product.

49-mer and 70-mer extension products and the dinucleotide cleavage secondary amplification product were observed only in the presence of M.tb target DNA (samples 1–3, indicating extension of the signal primer and transformation to double-stranded form. In the absence of M.tb DNA no secondary amplification products (extension products or cleavage products) were observed.

The $^{32}$P-dinucleotide cleavage product was alternatively detected by liquid scintillation counting. SDA was repeated in the presence of 0.5 nM 5'-$^{32}$P-labeled SEQ ID NO:6 signal primer. Prior to its use in SDA, the $^{32}$P-labeled signal primer was purified away from the gamma-$^{32}$P-ATP used in the kinase labeling reaction by denaturing gel electrophoresis. $S_1$ and $S_2$ were present at 180 and 30 nM. Exonuclease deficient Klenow was used at 0.25 units. SDA was performed for 3 hrs. Samples 1–7 contained $10^5$, $10^4$, $10^3$, $10^2$, 10, 1 and 0 M.tb genome molecules. After SDA, 40 units of EcoRI were added to each SDA reaction and the samples were incubated at 37° C. for 30 min.

A 12.5 μl aliquot from each 50 μl SDA reaction was diluted to 75 μl in 20 mM TRIS-HCL (pH 7.4), 50 mM KCl, 5 mM $MgCl_2$. Each of these samples was then filtered using a MICROCON-10 microconcentrator (icon, Beverly, Mass.) and $^{32}P$ activity was detected in the filtrate and on the filter by liquid scintillation counting. The results are shown below:

| Sample | Initial # of M tb Genome Molecules | Filtrate (cpm) | Filter (cpm) |
|---|---|---|---|
| 1 | $10^5$ | 13,449 | 44,802 |
| 2 | $10^4$ | 12,299 | 49,366 |
| 3 | $10^3$ | 9,006 | 50,739 |
| 4 | $10^2$ | 6,689 | 52,712 |
| 5 | 10 | 3,153 | 57,732 |
| 6 | 1 | 2,072 | 55,835 |
| 7 | 0 | 2,120 | 57,995 |

The $^{32}P$-dinucleotide released by EcoRI cleavage of the double-stranded 70-mer extension product is small enough that it passes through the MICROCON-10 filter, while the larger initial $^{32}P$-labeled 33-mer signal primer and $^{32}P$-labeled 49-mer extension product are retained on the filter. Using this filtration detection method, the IS6110 target sequence could be detected in a sample which contained as few as 10 M.tb genomes prior to SDA.

EXAMPLE 3

Two signal primers, one modified to facilitate capture and one modified to facilitate detection, were used to generate secondary amplification products in an SDA reaction. In this experiment, one signal primer had an affinity ligand (Q', three biotin moieties) attached to its 5' end and the second signal primer was 5'-end labeled with a reporter group (R, a $^{32}P$-containing phosphate group). Thus, double-stranded secondary amplification products which comprised both the reporter group and the affinity ligand (such as structure #3 and structure #9 of FIG. 1A and FIG. 1B) could be captured and detected. In this example, streptavidin coated magnetic beads were used to capture and separate the secondary amplification products, which were then detected by scintillation counting.

Biotinylated signal primers were prepared as follows. Oligonucleotide SEQ ID NO:7 was synthesized on an Applied Biosystems DNA Synthesizer Model 380B, using standard phosphoramidite chemistry. The instrument was then used to attach three biotin groups to the oligonucleotide by three successive couplings with BIOTIN ON phosphoramidite (Clonetech). Following synthesis, the oligonucleotide was deprotected by treatment with concentrated ammonia and purified by denaturing gel electrophoresis. The biotinylated signal primers with attached affinity ligands for capture of the secondary amplification products are referred to as capture signal primers and, for the purposes of this example, are analogous to the Q'-C' signal primer of FIG. 1A and FIG. 1B wherein Q' comprises biotin.

To prepare $^{32}P$-labeled signal primers, oligonucleotides SEQ ID NO:1 and SEQ ID NO:8 were labeled with radioactive phosphate as described by Walker, et al. (1992, Nucl. Acids Res., supra). The radiolabeled signal primers are referred to as detection signal primers and, for the purposes of this example, are analogous to the R-B signal primer of FIG. 1A and FIG. 1B wherein R comprises a radiolabel. In the experiment, one of these two detection signal primers was used in conjunction with the capture signal primer to generate secondary amplification products.

SDA was carded out essentially as described by Walker, et al. (1992, Nucl. Acids Res., supra) with the following modifications. Amplification primers were SEQ ID NO:9 and SEQ ID NO:10 (analogous to A and D' in FIG. 1A and FIG. 1B). These primers amplify a 103 nucleotide fragment (nucleotide positions 944–1046) of the IS6110 insertion element of M.tb. Each 50 μl reaction contained the following components: 45 mM $K_rPO_4$, pH 7.5; 6 mM $MgCl_2$; 0.1 mg/ml acetylated BSA; 12% dimethylsulfoxide; 0.5 mM dUTP; 0.2 mM each dCTP, dGTP, dATPαS; 500 nM amplification primers: 50 nM bumper primers (SEQ ID NO:11 and SEQ ID NO:12); 75 nM detection signal primer and capture signal primer (SEQ ID NO:1 and SEQ ID NO:7 or SEQ ID NO:8 and SEQ ID NO:7); 100 ng human placental DNA; 150 units HincII (New England Biolabs); 2.5 units exo⁻ Klenow DNA polymerase (US Biochemicals); 3% (v/v) glycerol added with enzymes; and either 0 or $10^5$ copies of the M.tb genome.

All reaction components, except $MgCl_2$, HincII and polymerase, were assembled and the mixtures were heated to 95° C. for two minutes. The samples were then placed in a water bath at 40° C. for two minutes, 3 μl of 0.1M $MgCl_2$ were added to each sample and the samples were mixed. Three μl of an enzyme mixture containing 50 units/μl HincII, 0.833 units/μl polymerase and 50% (v/v) glycerol were added and the samples were incubated at 40° C. for 2 hrs.

After incubation, a 5 μl aliquot of each reaction mixture was analyzed by denaturing gel electrophoresis. Because detection on gels requires only the presence of R, various products appeared in the range of 50–120 nucleotides for samples containing genomic M.tb DNA. These bands were absent in reactions lacking M.tb DNA, indicating that the reaction products in this size range were target-specific. The secondary amplification products predicted for this example, determined by calculation of the known sizes and binding positions of the signal primers according to the reaction scheme outlined in FIG. 1A and FIG. 1B, are shown in the following Table. As can be seen from FIG. 1A and FIG. 1B, structure #3 (in single-stranded form on denaturing gels) contains R and is detectable. In addition, the detectable single strand of structure #3 is identical to structure #2 and to the detectable single strand of structure #9. These secondary amplification products are therefore indistinguishable on the gel. Structure #4 and structure #5 (also in single-stranded form on denaturing gels) are also detectable by virtue of the presence of R.

EXPECTED SECONDARY PRODUCT SIZES (nucleotides, nt)

| | $^{32}P$-Labeled Signal Primer | |
|---|---|---|
| Structure (FIGS. 1A and 1B) | SEQ ID NO 1 | SEQ ID NO 8 |
| #3, #9 and #8 | 52 nt | 92 nt |
| #4 | 58 nt | 98 nt |
| #5 | 79 nt | 119 nt |

Streptavidin-coated magnetic beads (Streptavidin Paramagnetic Particles, Nucleic Acid Qualified, 1 mg/ml, Promega Corporation, Madison, Wis.) were washed three times with 1X PBS as recommended by the manufacturer.

For each analysis, 50 μg of the beads were suspended in 180 μl of 1X PBS in a 1.5 ml eppendorf tube and combined with 20 μl of the SDA reaction mixture. These samples were incubated with occasional mixing for 10 min. at room temperature. A magnet was then used to gather the beads on one side of the tube and the supernatant was removed. The beads were then washed by resuspending them in 1X PBS (200 μl), gathering them magnetically on the side of the tube and removing the supernatant. This washing process was repeated three more times, and the $^{32}P$ activity remaining on the beads was detected by liquid scintillation counting. The results are shown in the following Table:

| Detector Signal Primer | $10^5$ Initial Genome Molecules | 0 Initial Genome Molecules |
|---|---|---|
| SEQ ID NO 1 | 80,547 cpm | 1,080 cpm |
| SEQ ID NO 8 | 54,385 cpm | 961 cpm |

Small aliquots of the beads (10%), removed prior to scintillation counting, were heated to 95° C. in the presence of 50% urea and subjected to electrophoresis on a denaturing polyacrylamide gel. Only structure #3 and structure #9 contain both the biotin modification and the $^{32}P$ label, and it was predicted that only these structures would bind to the beads and be detectable. Autoradiography of the gel did show that the structure #3 and structure #9 secondary amplification products represent the predominant radioactive species retained by the beads during the magnetic separation process. However, smaller amounts of a species corresponding to structure #1 also appeared on the autoradiogram. It is possible that structure #1, produced by extension of the detector signal primer, may be captured when hybridized to a Q'-C' capture signal primer (prior to capture signal primer extension and generation of structure #2; see the reaction step following structure #1 in FIG. 1A). Although small amounts of structure # 1 were apparently captured and detected in addition to the predicted structures #3 and #9, all captured and detected secondary amplification products were target specific and did not appear in samples lacking genomic M.tb DNA.

The background radioactivity detected on the beads in the absence of M.tb DNA (0 initial genome molecules) appears to be due to nonspecific binding of unreacted detector signal primers. Electrophoretic analysis of beads from these samples showed that the only radioactive material present was a very faint band corresponding to the detector signal primers, even after overnight exposure of the autoradiogram. However, the secondary amplification products were clearly detected above these background levels of signal.

SEQUENCE LISTING

```
<160> NUMBER OF SEQ ID NOS: 25

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

caatgttgtt ccttgaggaa gttg                                          24


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

gttgttcctt gaggaagttg                                               20


<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

gttccttgag gaagttg                                                  17


<210> SEQ ID NO 4
<211> LENGTH: 41
```

-continued

<212> TYPE: DNA
<213> ORGANISM: Artificial Sequence
<220> FEATURE:
<223> OTHER INFORMATION: Description of Artificial Sequence: Synthetic
primer

<400> SEQUENCE: 4 cgattccgct ccagacttct cgggaacaaa gaaggcatcg t 41

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5 accgcatcga atgcatgtct cgggtggcag cattgttatt a 41

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 6 acgttagcca ccatacggat acccaaagac cacattggca 40

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7 actgatccgc actaacgact acccaaagac cacacggact 40

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8 acgttagcca ccatacttga acccaaagac cacattggca 40

<210> SEQ ID NO 9
<211> LENGTH: 126
<212> TYPE: DNA
<213> ORGANISM: Human Severe Acute Respitory Syndrome Coronavirus

<400> SEQUENCE: 9 aacaaagaag gcatcgtatg ggttgcaact gagggagcct tgaatacacc caaagaccac 60 attggcaccc gcaatcctaa taacaatgct gccaccgtgc tacaacttcc tcaaggaaca 120 acattg 126

<210> SEQ ID NO 10
<211> LENGTH: 126

-continued

<212> TYPE: RNA
<213> ORGANISM: Human Severe Acute Respitory Syndrome Coronavirus

<400> SEQUENCE: 10 aacaaagaag gcaucguaug gguugcaacu gagggagccu ugaauacacc caaagaccac 60 auuggcaccc gcaauccuaa uuacaaugcu gccaccgugc uacaacuucc ucaaggaaca 120 acauug 126

<210> SEQ ID NO 11
<211> LENGTH: 126
<212> TYPE: DNA
<213> ORGANISM: Human Severe Acute Respitory Syndrome Coronavirus

<400> SEQUENCE: 11 aacaaagaag gcatcgtatg ggttgcaact gagggagcct tgaatacacc caaagaccac 60 acggactccc gcaatcctaa ttacaatgct gccaccgtgc tacaacttcc tcaaggaaca 120 acattg 126

<210> SEQ ID NO 12
<211> LENGTH: 126
<212> TYPE: RNA
<213> ORGANISM: Human Severe Acute Respitory Syndrome Coronavirus

<400> SEQUENCE: 12 aacaaagaag gcaucguaug gguugcaacu gagggagccu ugaauacacc caaagaccac 60 acggacuccc gcaauccuaa uuacaaugcu gccaccgugc uacaacuucc ucaaggaaca 120 acauug 126

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
probe

<400> SEQUENCE: 13 tcccgagtac gttagccacc atacggat 28

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
probe

<400> SEQUENCE: 14 acccgagtag ctatccgcca taagccat 28

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 15 tccccgagta cgttagccac catacttga 29

-continued

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 16 tccccgagta ctgatccgca ctaacgact 29

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17 atgttcccga aggtgtgact tc 22

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18 cgattccgct ccagacttct cgggacaagg aactgattac a 41

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19 accgcatcga atgcatgtct cgggtgcgtg acattccaaa g 41

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20 acgttagcca ccatacggat caatttgctc caagtgcctc 40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21 acgttagcca ccatacttga caatttgctc caagtgcctc 40

<210> SEQ ID NO 22

-continued

```
<211> LENGTH: 111
<212> TYPE: DNA
<213> ORGANISM: Human Severe Acute Respitory Syndrome Coronavirus

<400> SEQUENCE: 22

gacaaggaac tgattacaaa cattggccgc aaattgcaca atttgctcca agtgcctctg     60

cattctttgg aatgtcacgc attggcatgg aagtcacacc ttcgggaaca t             111


<210> SEQ ID NO 23
<211> LENGTH: 111
<212> TYPE: RNA
<213> ORGANISM: Human Severe Acute Respitory Syndrome Coronavirus

<400> SEQUENCE: 23

gacaaggaac ugauuacaaa cauuggccgc aaauugcaca auuugcucca agugccucug     60

cauucuuugg aaugucacgc auuggcaugg aagucacacc uucgggaaca u             111


<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

gcctcttcgc tatta                                                      15


<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

agctatccgc cataagccat acccaaagac cacacggact                           40
```

What is claimed is:

1. A method for concurrently generating a secondary amplification product and an amplification product in a Strand Displacement Amplification (SDA) reaction, wherein the SDA reaction comprises (i) a DNA polymerase having strand displacing activity and lacking 5'-3' exonuclease activity and (ii) a restriction endonuclease which nicks a hemimodified double stranded restriction endonuclease recognition site, the method comprising:

a) hybridizing a signal primer to a target sequence and hybridizing a first SDA amplification primer to the target sequence upstream of the signal primer;

b) extending the hybridized signal primer on the target sequence to produce a signal primer extension product and extending the hybridized first SDA amplification primer on the target sequence such that extension of the first SDA amplification primer displaces the signal primer extension product from the target sequence;

c) hybridizing a second SDA amplification primer to the signal primer extension product and extending the hybridized second SDA amplification primer on the signal primer extension product to produce a second SDA amplification primer extension product comprising a newly synthesized strand and double stranded hemimodified recognition site for the restriction endonuclease;

d) nicking the hemimodified recognition site and displacing the newly synthesized strand from the signal primer extension product using the DNA polymerase;

e) hybridizing the signal primer to the displaced newly synthesized strand and extending the signal primer such that a double stranded secondary amplification product is generated.

2. The method of claim 1 further comprising detecting the secondary amplification product by means of a chemical modification or special nucleotide sequence incorporated into the signal primer.

3. The method of claim 2 wherein the secondary amplification product is detected by means of an affinity ligand or reporter group incorporated into the signal primer.

4. The method of claim 2 wherein the secondary amplification product is detected by means of a nucleotide sequence incorporated into the signal primer, the nucleotide sequence comprising a recognition site for a double-stranded DNA binding protein.

5. The method of claim 2 wherein the secondary amplification product is detected by means of a nucleotide sequence incorporated into the signal primer, the nucleotide sequence comprising a restriction endonuclease recognition site.

6. The method of claim 5 wherein the secondary amplification product is detected by cleaving the restriction endonuclease recognition site with a restriction endonuclease to generate a cleavage product, separating the cleavage product on the basis of size and detecting the cleavage product.

7. The method of claim 6 wherein the cleavage product is separated by filtration.

8. A method for concurrently generating a secondary amplification product and an amplification product in a Strand Displacement Amplification (SDA) reaction, wherein the SDA reaction comprises (i) a DNA polymerase having strand displacing activity and lacking 5'-3' exonuclease activity and (ii) a restriction enzyme which nicks a hemi-modified double stranded restriction endonuclease recognition site, the method comprising:

a) hybridizing a first signal primer to a first strand of a double-stranded target sequence and hybridizing a first SDA amplification primer to the first strand of the target sequence upstream of the first signal primer;

b) extending the hybridized first signal primer on the first strand to produce a first extension product and extending the hybridized first SDA amplification primer on the first strand such that extension of the first SDA amplification primer displaces the first extension product from the target sequence;

c) hybridizing a second signal primer to the first extension product and hybridizing a second SDA amplification primer to the first extension product upstream of the second signal primer;

d) extending the hybridized second signal primer on the first extension product to produce a second SDA extension product and extending the hybridized second amplification primer on the first extension product such that extension of the second SDA amplification primer displaces the second extension product from the first extension product;

e) hybridizing the first signal primer to the displaced second extension product and extending the hybridized first signal primer on the second extension product such that a double stranded secondary amplification product is generated.

9. The method of claim 8 further comprising detecting the secondary amplification product by means of a reporter group incorporated into the first signal primer and a modification to facilitate capture of the secondary amplification product incorporated into the second signal primer.

10. The method of claim 8 further comprising the steps of:

a) hybridizing the second SDA signal primer to a second strand of the double stranded target sequence and hybridizing the second amplification primer to the second strand of the target sequence upstream of the second signal primer;

b) extending the hybridized second signal primer on the second strand to produce a third extension product and extending the hybridized second SDA amplification primer on the second SDA strand such that extension of the second amplification primer displaces the third extension product from the second strand of the target sequence;

c) hybridizing the first signal primer to the displaced third extension product and hybridizing the first SDA amplification primer to the displaced third extension product upstream of the first signal primer;

d) extending the hybridized first signal primer on the third extension product to produce a fourth extension product and extending the hybridized first SDA amplification primer on the third extension product such that extension of the first SDA amplification primer displaces the fourth extension product from the third extension product;

e) hybridizing the second signal primer to the displaced fourth extension product and extending the second signal primer on the fourth extension product such that a double stranded secondary amplification product is generated.

11. The method of claim 10 further comprising detecting the secondary amplification product by means of a chemical modification or special nucleotide sequence incorporated into the signal primer.

12. The method of claim 11 wherein the secondary amplification product is detected by means of an affinity ligand or reporter group incorporated into the signal primer.

13. The method of claim 11 wherein the secondary amplification product is detected by means of a nucleotide sequence incorporated into the signal primer, the nucleotide sequence comprising a recognition site for a double-stranded DNA binding protein.

14. The method of claim 11 wherein the secondary amplification product is detected by means of a nucleotide sequence incorporated into the signal primer, the nucleotide sequence comprising a restriction endonuclease recognition site.

15. The method of claim 14 wherein the secondary amplification product is detected by cleaving the restriction endonuclease recognition site with a restriction endonuclease to generate a cleavage product, separating the cleavage product on the basis of size and detecting the cleavage product.

16. The method of claim 15 wherein the cleavage product is separated by filtration.

17. The method of claim 2 wherein the secondary amplification products are detected in concurrently with amplification of the target sequence in real-time.

18. The method of claim 2 wherein the secondary amplification products are detected post-amplification.

19. The method of claim 9 wherein the secondary amplification products are detected in concurrently with amplification of the target sequence in real-time.

20. The method of claim 9 wherein the secondary amplification products are detected post-amplification.

*21. A method for concurrently generating a secondary amplification product and an amplification product in a primer based nucleic acid amplification reaction, the method comprising:*

*a) hybridizing a signal primer to a target sequence and hybridizing a first amplification primer to the target sequence upstream of the signal primer, wherein a characteristic of said signal primer is that it may function as an amplifiable primer in a linear fashion;*

*b) extending the hybridized signal primer on the target sequence to produce a signal primer extension product and extending the hybridized first amplification primer on the target sequence such that extension of the first amplification primer displaces the signal primer extension product from the target sequence;*

*c) hybridizing a second amplification primer to the signal primer extension product and extending the hybridized second amplification primer on the signal primer extension product to produce a second amplification primer extension product comprising a newly synthesized strand;*

*d) displacing the newly synthesized strand from the signal primer extension product; and*

*e) hybridizing the signal primer to the displaced newly synthesized strand and extending the signal primer*

*such that a double stranded secondary amplification product is generated.*

*22. The method of claim 21 further comprising detecting the secondary amplification product by means of a chemical modification or special nucleotide sequence incorporated into the signal primer.*

*23. The method of claim 22 wherein the secondary amplification product is detected by means of an affinity ligand or reporter group incorporated into the signal primer.*

*24. The method of claim 22 wherein the secondary amplification product is detected by means of a nucleotide sequence incorporated into the signal primer, the nucleotide sequence comprising a recognition site for a double-stranded DNA binding protein.*

*25. The method of claim 22 wherein the secondary amplification product is detected by means of a nucleotide sequence incorporated into the signal primer, the nucleotide sequence comprising a restriction endonuclease recognition site.*

*26. The method of claim 25 wherein the secondary amplification product is detected by cleaving the restriction endonuclease recognition site with a restriction endonuclease to generate a cleavage product.*

*27. The method of claim 26 wherein the secondary amplification product is detected by separating the cleavage product on the basis of size and detecting the cleavage product.*

*28. The method of claim 27 wherein the cleavage product is separated by filtration.*

*29. A method for concurrently generating a secondary amplification product and an amplification product in a primer based nucleic acid amplification reaction, the method comprising:*

*a) hybridizing a first signal primer to a first strand of a double-stranded target sequence and hybridizing a first amplification primer to the first strand of the target sequence upstream of the first signal primer, wherein a characteristic of said signal primer is that it may function as an amplifiable primer in a linear fashion;*

*b) extending the hybridized first signal primer on the first strand to produce a first extension product and extending the hybridized first amplification primer on the first strand such that extension of the first amplification primer displaces the first extension product from the target sequence;*

*c) hybridizing a second signal primer to the first extension product and hybridizing a second amplification primer to the first extension product upstream of the second signal primer;*

*d) extending the hybridized second signal primer on the first extension product to produce a second extension product and extending the hybridized second amplification primer on the first extension product such that extension of the second amplification primer displaces the second extension product from the first extension product; and*

*e) hybridizing the first signal primer to the displaced second extension product and extending the hybridized first signal primer on the second extension product such that a double stranded secondary amplification product is generated.*

*30. The method of claim 29 further comprising detecting the secondary amplification product by means of a reporter group incorporated into the first signal primer and a modification to facilitate capture of the secondary amplification product incorporated into the second signal primer.*

*31. The method of claim 29 further comprising:*

*a) hybridizing the second signal primer to a second strand of the double stranded target sequence and hybridizing the second amplification primer to the second strand of the target sequence upstream of the second signal primer;*

*b) extending the hybridized second signal primer on the second strand to produce a third extension product and extending the hybridized second amplification primer on the second strand such that extension of the second amplification primer displaces the third extension product from the second strand of the target sequence;*

*c) hybridizing the first signal primer to the displaced third extension product and hybridizing the first amplification primer to the displaced third extension product upstream of the first signal primer;*

*d) extending the hybridized first signal primer on the third extension product to produce a fourth extension product and extending the hybridized first amplification primer on the third extension product such that extension of the first amplification primer displaces the fourth extension product from the third extension product; and*

*e) hybridizing the second signal primer to the displaced fourth extension product and extending the second signal primer on the fourth extension product such that a double stranded secondary amplification product is generated.*

*32. The method of claim 31 further comprising detecting the secondary amplification product by means of a chemical modification or special nucleotide sequence incorporated into the signal primer.*

*33. The method of claim 32 wherein the secondary amplification product is detected by means of an affinity ligand or reporter group incorporated into the signal primer.*

*34. The method of claim 32 wherein the secondary amplification product is detected by means of a nucleotide sequence incorporated into the signal primer, the nucleotide sequence comprising a recognition site for a double-stranded DNA binding protein.*

*35. The method of claim 32 wherein the secondary amplification product is detected by means of a nucleotide sequence incorporated into the signal primer, the nucleotide sequence comprising a restriction endonuclease recognition site.*

*36. The method of claim 35 wherein the secondary amplification product is detected by cleaving the restriction endonuclease recognition site with a restriction endonuclease to generate a cleavage product.*

*37. The method of claim 36 wherein the secondary amplification product is detected by separating the cleavage product on the basis of size and detecting the cleavage product.*

*38. The method of claim 37 wherein the cleavage product is separated by filtration.*

*39. The method of claim 22 wherein the secondary amplification products are detected in real-time.*

*40. The method of claim 22 wherein the secondary amplification products are detected post-amplification.*

*41. The method of claim 29 wherein the secondary amplification products are detected in real-time.*

*42. The method of claim 29 wherein the secondary amplification products are detected post-amplification.*

* * * * *